United States Patent
Scully et al.

(10) Patent No.: US 6,795,777 B1
(45) Date of Patent: Sep. 21, 2004

(54) IDENTIFYING MOLECULES OF A SAMPLE

(75) Inventors: Marlan O. Scully, Bryan, TX (US); George W. Kattawar, College Station, TX (US); Robert P. Lucht, West Lafayette, IN (US); Tomas Opatrny, College Station, TX (US); Herschel S. Pilloff, Longmont, CO (US); Alexei V. Sokolov, College Station, TX (US); M. Suhail Zubairy, College Station, TX (US)

(73) Assignee: The Texas A&M University System, College Station, TX (US)

(*) Notice: Subject to any disclaimer, the term of this patent is extended or adjusted under 35 U.S.C. 154(b) by 0 days.

(21) Appl. No.: 10/379,519

(22) Filed: Mar. 4, 2003

Related U.S. Application Data

(60) Provisional application No. 60/361,399, filed on Mar. 4, 2002.

(51) Int. Cl.[7] .................. G01N 31/00; G01J 3/44
(52) U.S. Cl. ............... 702/28; 702/27; 250/251; 250/493.1; 356/301; 356/302
(58) Field of Search .................. 702/27, 28, 75, 702/79; 250/251, 339.06, 339.11, 493.1; 356/301–302, 336–338

(56) References Cited

U.S. PATENT DOCUMENTS

| | | | | |
|---|---|---|---|---|
| 4,405,237 A | * | 9/1983 | Manuccia et al. | 356/301 |
| 6,180,415 B1 | * | 1/2001 | Schultz et al. | 436/518 |
| 6,469,781 B1 | * | 10/2002 | Katz et al. | 356/37 |
| 6,675,106 B1 | * | 1/2004 | Keenan et al. | 702/28 |

* cited by examiner

*Primary Examiner*—Bryan Bui
(74) *Attorney, Agent, or Firm*—Baker Botts L.L.P.

(57) ABSTRACT

According to one embodiment of the present invention, identifying a molecule of a sample includes illuminating the sample with a preparation light beam, where the preparation light beam can initiate a substantially maximized coherence of a target molecule to yield a molecular signature corresponding to the target molecule. The sample is illuminated with a probe light beam, where the probe light beam can scatter radiation from the sample. Radiation scattered from the sample is detected, and whether the radiation exhibits the molecular signature is determined. The target molecule is identified in accordance with the determination of whether the radiation exhibits the molecular signature.

20 Claims, 3 Drawing Sheets

US 6,795,777 B1

IDENTIFYING MOLECULES OF A SAMPLE

RELATED APPLICATION

This application claims benefit under 35 U.S.C. § 119(e) of U.S. Provisional Application Serial No. 60/361,399, entitled "FAST CARS: DEVELOPING A LASER SPECTROSCOPIC TECHNIQUE FOR RAPID IDENTIFICATION OF BACTERIAL SPORES," filed Mar. 4, 2002.

TECHNICAL FIELD OF THE INVENTION

This invention relates generally to the field of laser spectroscopy and more specifically to identifying molecules of a sample.

BACKGROUND OF THE INVENTION

Molecules such as dipicolinic acid molecules of airborne bacterial spores may be identified by techniques using microscopic, chemical, or biological assays. These techniques, however, may be time consuming. Faster analysis may be performed using laser spectroscopy techniques. These techniques, however, may not be able to provide precise identification of molecules. Consequently, known techniques for identifying molecules may be unsatisfactory in certain situations.

SUMMARY OF THE INVENTION

In accordance with the present invention, disadvantages and problems associated with previous techniques for identifying molecules may be reduced or eliminated.

According to one embodiment of the present invention, identifying molecules of a sample includes illuminating the sample with a preparation light beam, where the preparation light beam can initiate a substantially maximized coherence of a target molecule to yield a molecular signature corresponding to the target molecule. The sample is illuminated with a probe light beam, where the probe light beam can scatter radiation from the sample. Radiation scattered from the sample is detected, and whether the radiation exhibits the molecular signature is determined.

Certain embodiments of the invention may provide one or more technical advantages. A technical advantage of one embodiment may be that a sample with target molecules is illuminated with a preparation light beam to yield a substantially maximized coherence for the target molecules. The target molecules are identified in accordance with radiation scattered from the sample as a Raman scattering signal. By producing substantially maximized coherence, the Raman scattering signal may be enhanced to provide for more effective identification of the target molecules.

Certain embodiments of the invention may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION OF THE DRAWINGS

Embodiments of the present invention and its advantages are best understood by referring to FIGS. 1 through 6 of the drawings, like numerals being used for like and corresponding parts of the various drawings.

Figure 1:
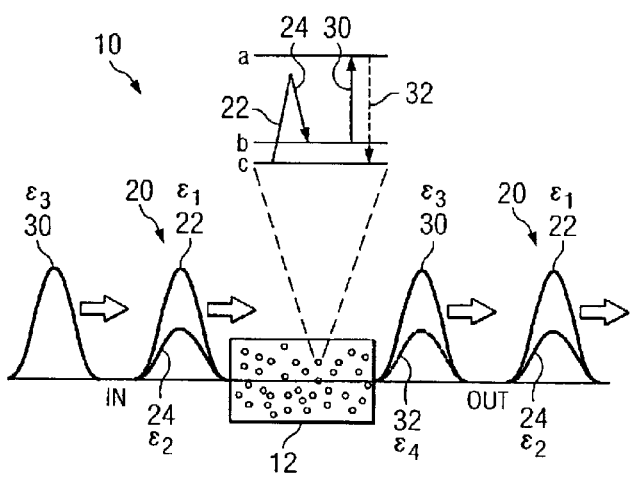
FIG. 1 is a diagram illustrating one embodiment of a procedure for identifying a target molecule.

FIG. 1 is a diagram 10 illustrating one embodiment of a procedure for identifying a target molecule. According to the embodiment, the target molecule may be identified according to a femtosecond adaptive spectroscopic technique for coherent anti-Stokes Raman spectroscopy (FAST CARS). Spectra resulting from anti-Stokes radiation are typically different for different molecular species, and thus may be used to identify target molecules.

According to one aspect of operation, a preparation light beam 20 comprising a pulse 22 having an amplitude $\epsilon_1$ and a pulse 24 having an amplitude $\epsilon_2$ illuminates a sample 12. The pulse shape of preparation light beam 20 may be selected to produce substantially maximized coherence of a target molecule in order to generate a molecular signature such as a characteristic spectrum. The maximized coherence may be produced between a first vibrationally excited state |b) and a ground state |c) of the target molecule.

A probe light beam 30 having an amplitude $\epsilon_3$ is scattered from the oscillating molecules of sample 12 to excite the molecules to an electronically excited state |a). In response, an anti-Stokes radiation 32 is emitted. If the characteristic spectrum is detected, the target molecules are present. By producing maximized coherence at a target molecule, a Raman scattering signal of anti-Stokes radiation 32 may be enhanced to provide for more effective analysis of the target molecule.

According to one embodiment, sample 12 comprises particles that include target molecules of interest and other particles such as dust particles. Target molecules may include, for example, dipicolinic acid (DPA) typical of endospores. Endospores include dipicolinic acid and its corresponding salt in a living core that may provide a signature for endospores.

Preparation light beam 20 induces a maximized coherence such as maximized ground-state coherence of sample 12 to enhance a Raman scattering signal. In a state of maximal coherence, each molecule oscillates with substantially the same phase so that the molecules oscillate substantially in unison. "Each" as used in this document refers to each member of a set or each member of a subset of a set. In known techniques, the coherence is not maximized.

Preparation light beam 20 may comprise femtosecond pulse sequences for which phase coherence exists between the individual pulses. The individual pulses need not be strong, since mainly the collective effect of the pulses is used. The femtosecond pulses may be chained in picosecond to nanosecond pulse sequences. To avoid dissipation of molecular coherence, ultra-short pulses may be used to generate coherence at a time scale that is small compared with the molecular relaxation time.

Probe light beam 30 initiates Raman scattering within sample 12 to yield anti-Stokes field 32. Probe light beam 30 may comprise, for example, a higher frequency visible light or ultraviolet light. Raman scattering refers to an inelastic scattering of electromagnetic fields from vibrating molecules, resulting in a change in frequency. Radiation with frequency $v_1$ scatters inelastically off vibrating molecules, resulting in a scattered radiation with frequency $v_2 = v_1 + \omega_{bc}$, where $\omega_{bc}$ refers to the frequency of the molecular vibrations. Radiation with down-shifted frequency $v_2$ is the Stokes field, and radiation with up-shifted frequency is the anti-Stokes field.

Resonant Raman scattering occurs when the frequency of the incident radiation coincides with one of the electron transitions, and is typically richer than the non-resonant Raman scattering. Resonant Raman radiation may be governed by the oscillating dipole between states |a) and |b) of the Stokes case, states |a) and |c) of the anti-Stokes case, or both.

The Raman scattering signal of resonant Raman scattering is relatively strong, and may be up to a million times stronger than the signal of non-resonant Raman scattering. Moreover, typically only the Raman lines corresponding to very few vibrational modes associated with strongly absorbing locations of a molecule exhibit the large intensity enhancement. The resonance Raman spectra, however, may be contaminated with fluorescence. To avoid fluorescence contamination, ultraviolet light may be used so that most of the fluorescence appears at much longer wavelengths than the Raman scattered radiation and may be filtered out.

Known techniques such as fluorescence spectroscopy may be used to select dust particles from particles of interest. Fluorescence spectroscopy, however, cannot differentiate among certain particles of interest. For example, fluorescence spectroscopy cannot distinguish between endospores and other organic particles. In contrast, the procedure of FIG. 1 may be used to identify target particles.

Figure 2:
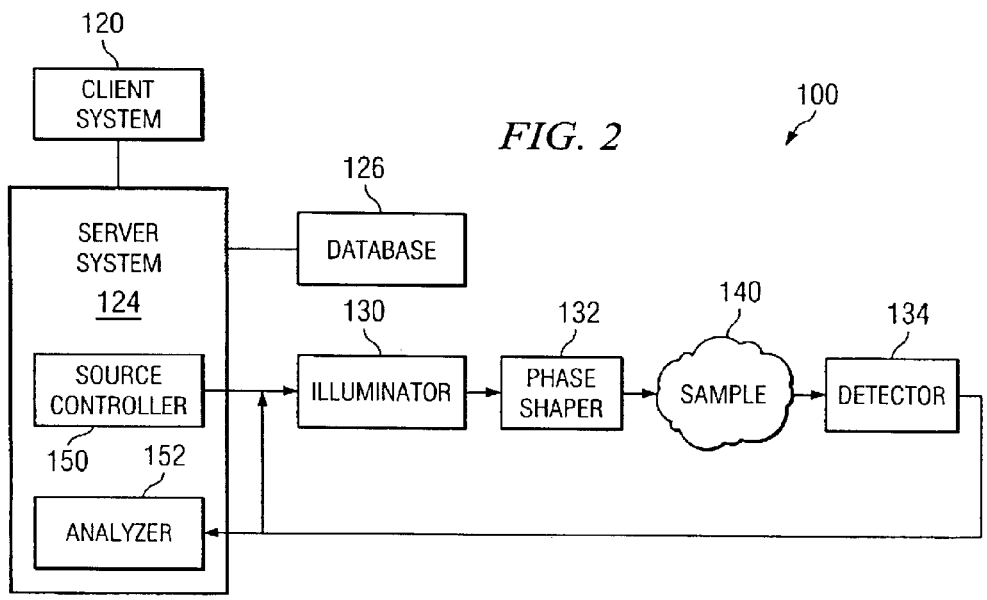
FIG. 2 is a block diagram of one embodiment of a system for identifying a target molecule.

FIG. 2 is a block diagram of one embodiment of a system 100 for identifying a target molecule. System 100 operates to control the shape of preparation light beam 20 in order to maximize ground-state coherence, which may enhance the Raman scattering signal and provide for more accurate identification of a target molecule. According to the illustrated embodiment, system 100 includes a client system 120, a server system 124, a database 126, an illuminator 130, a phase shaper 132, and a detector 134 that may be used to analyze sample 12. Server system 124 may include a source controller 150 and an analyzer 152.

According to one aspect of operation, source controller 150 instructs illuminator 130 and phase shaper 132 to generate preparation light beam 20 that produces maximized coherence of target molecules of sample 12. Source controller 150 also instructs illuminator 130 and phase shaper 132 to generate probe light beam 30 that initiates a Raman scattering radiation that exhibits a molecular signature characteristic of the target molecules. Detector 134 detects the molecular signature that analyzer 152 uses to identify the target molecules. Detector 134 may also provide source controller 150 with feedback information that source controller 150 may use to adjust preparation light beam 20 and/or probe light beam 30 in order to produce maximized coherence at sample 12.

According to one embodiment, source controller 150 determines an optimized shape of the pulse sequences required for the excitation of target molecules to yield maximized coherence. The frequency and amplitude of preparation light beam 20 may be adjusted. The central frequency and timing of probe light beam 30 may also be adjusted. Signal processing and data mining strategies may be used to adjust the signals. The shape may be dynamically adjusted in response to feedback from detector 134 to determine optimal pulse shapes. Any suitable search procedure such as adaptive evolutionary algorithms may be used to dynamically adjust the shape.

Source controller 150 may initiate maximized coherence according to any suitable procedure. Examples of procedures are described in more detail with reference to FIGS. 3, 4, and 5.

Figure 3:
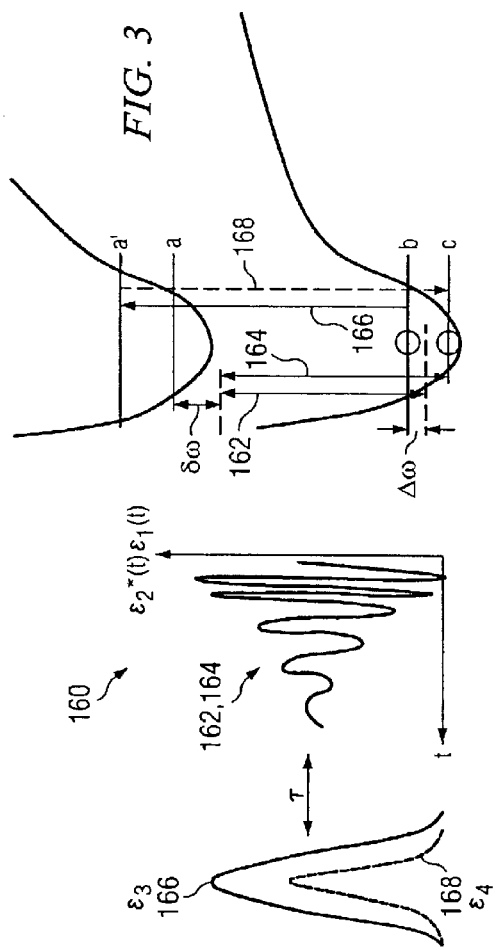
FIG. 3 is an energy level diagram illustrating one embodiment of a procedure for generating maximized coherence using a detuning frequency.

FIG. 3 is an energy level diagram 160 illustrating one embodiment of a procedure for generating maximized coherence using a detuning frequency $\delta\omega$. According to the embodiment, a field 162 having an amplitude $\epsilon_1$ and a field 164 having an amplitude $\epsilon_2$ are used to generate a maximized coherence $\rho_{bc}$ between states |b) and |c). Fields 162 and 164 may be off-resonant with an electronic detuning frequency $\delta\omega$ and optionally with a Raman detuning frequency $\Delta\omega$. A field 166 having an amplitude $\epsilon_3$ is used to initiate an anti-Stokes field 168 having an amplitude $\epsilon_4$.

If the excitation by fields 162 and 164 is applied resonantly where Raman detuning frequency $\Delta\omega$ is zero, the initial ground state |c) of the system is projected onto a new basis formed by the eigenvectors |+) and |−) and the system undergoes a sinusoidal Rabi flopping between states |b) and |c). A π/2 pulse may be applied to create maximum coherence $|\rho_{bc}|=0.5$. Alternatively, an excitation may be applied at a finite detuning frequency $\Delta\omega$ to allow the molecules initially at the ground state to follow the eigenstate |+) adiabatically.

Figure 4:
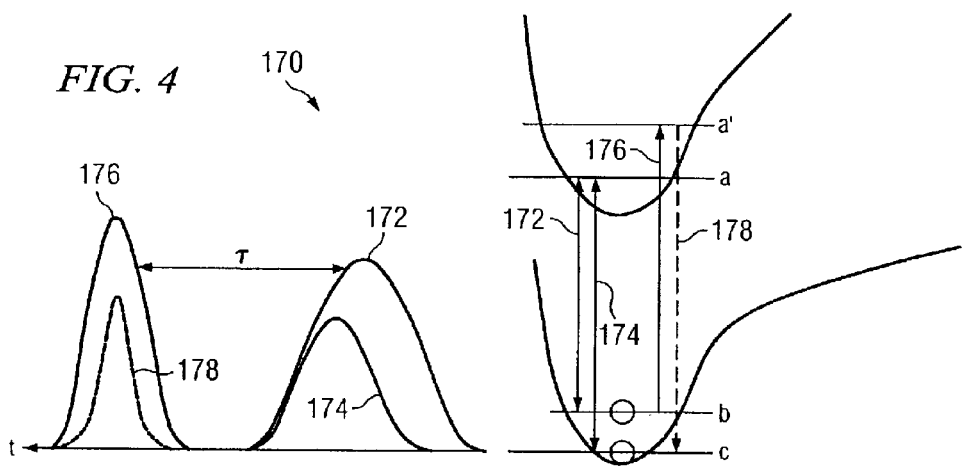
FIG. 4 is an energy level diagram illustrating one embodiment of a procedure for generating maximized coherence according to a stimulated Raman adibatic passage (STIRAP) procedure.

FIG. 4 is an energy level diagram 170 illustrating one embodiment of a procedure for generating maximized coherence according to a stimulated Raman adibatic passage (STIRAP) technique. According to the embodiment, counterintuitive pulses 172 and 174 having frequencies $\omega_{ab}$ and $\omega_{ac}$ are used to generate maximized coherence between states |b) and |c). After a time delay τ, a pulse 176 resonant with a |a'→|b) transition produces a signal 178 having a frequency $\omega_{a'c}$. In an all-resonant scheme where $\Delta\omega=\delta=0$, maximized coherence may be generated between states |b) and |c) such that the population of an upper state |a) may be substantially zero and fluorescence from upper state |a) may be reduced or eliminated.

Figure 5:
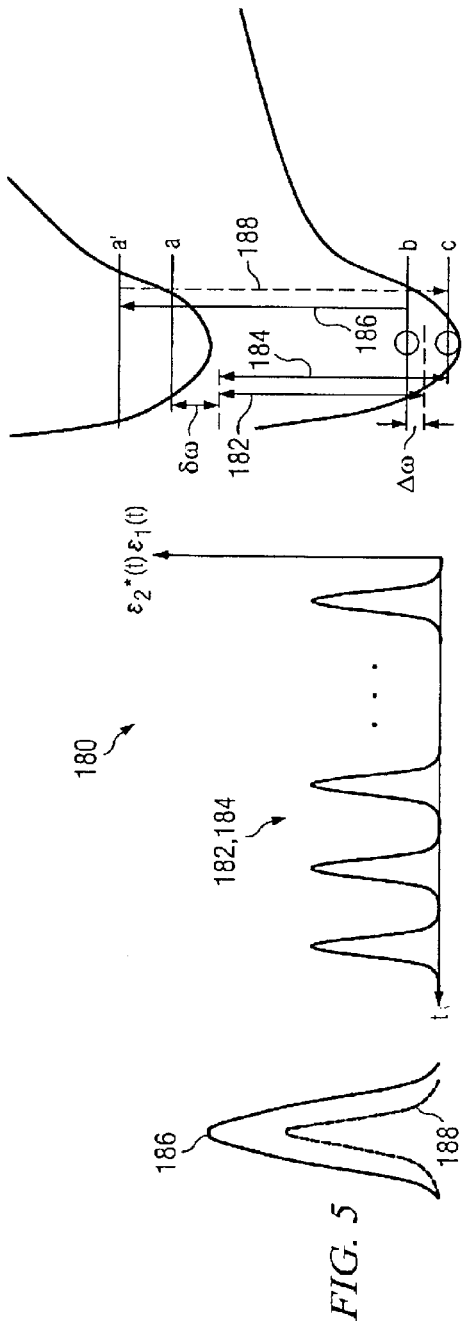
FIG. 5 is an energy level diagram illustrating one embodiment of a procedure for generating maximized coherence using a femtosecond pulse sequence.

FIG. 5 is an energy level diagram 180 illustrating one embodiment of a procedure for generating maximized coherence using a femtosecond pulse sequence. According to the embodiment, a femtosecond pulse sequence 182, 184 having a pulse 182 associated with an amplitude $\epsilon_1$ and a pulse 184 associated with an amplitude $\epsilon_2$ is used to initiate molecular motion $\rho_{bc}$ between states |b) and |c). A field 186 having an amplitude $\epsilon_3$ is used to generate an anti-Stokes field 188 having an amplitude $\epsilon_4$.

Referring back to FIG. 2, illuminator 130 generates light in response to instructions from source controller 150, and may comprise, for example, a laser such as a titanium sapphire laser. Short pulses may be generated by expanding the spectrum of a mode-locked laser by self-phase modulation of an optical waveguide. A diffraction grating and prism pairs may be used to compensate for group velocity dispersion.

Pulse shaper 132 shapes the amplitude and phase content of pulse sequences received from illuminator 130 in response to instructions from source controller 150, and may comprise, for example, a spatial light modulator in a 4f-arrangement. According to one embodiment, pulse shaper 32 disperses a spectrum into frequency components. Individual spectral amplitudes and phases of each frequency component may be independently adjusted using a spatial light modulator or an acoustic modulator. The spectrum is recombined into a single beam by a second dispersive element and directed towards sample 12. Pulse shaper 12 may provide for synthesis of arbitrarily shaped pulses at sample 12, and may avoid problems associated with dispersion of intermediate optical elements and windows.

Sample 12 includes particles that may include target particles. The particle may be pinned to a fixed surface and cooled to maximize the dephasing time T and narrow characteristic lines. The particle may be deflected by optical means such as laser tweezers or laser ionization and attached to a cooled conducting surface. Cooling the particle to liquid helium temperature may enhance the dephasing time from $T \leq 1$ picosecend at room temperature to perhaps a few picoseconds or more at a few degrees Kelvin.

Detector 134 detects radiation scattered from sample 12 and sends information describing the radiation to source controller 150 and analyzer 152. Detector 134 may comprise, for example, photomultiplier tube. Analyzer 152 analyzes the information to identify target molecules. For example, analyzer 152 may determine whether the scattered radiation exhibits a molecular signature such as a spectrum characteristic of a target molecule. If the scattered radiation exhibits the molecular signature, analyzer 12 may determine that the target molecule is present at sample 12.

Client system 120 and server system 124 may each operate on one or more computers and may include appropriate input devices, output devices, mass storage media, processors, memory, or other components for receiving, processing, storing, and communicating information according to the operation of system 100. As used in this document, the term "computer" refers to any suitable device operable to accept input, process the input according to predefined rules, and produce output, for example, a personal computer, work station, network computer, wireless telephone, personal digital assistant, one or more microprocessors within these or other devices, or any other suitable processing device.

Client system 120 and server system 124 may be integrated or separated according to particular needs. For example, the present invention contemplates the functions of both client system 120 and server system 124 being provided using a single computer system, for example, a single personal computer. If client system 120 and server system 124 are separate, client system 120 may be coupled to server system 124 using one or more local area networks (LANs), metropolitan area networks (MANs), wide area networks (WANs), a global computer network such as the Internet, or any other appropriate wire line, wireless, or other links.

A database 126 stores data that may be used by server system 124. Database 126 may be local to or remote from server system 124, and may be coupled to server system 124 using one or more local area networks (LANs), metropolitan area networks (MANs), wide area networks (WANs), a global computer network such as the Internet, or any other appropriate wire line, wireless, or other links.

Modifications, additions, or omissions may be made to system 100 without departing from the scope of the invention. For example, system 100 may be miniaturized as a device that may be carried. Moreover, the operation of the system may be performed by more or fewer modules.

For example, the operation of illuminator 130 and phase shaper 132 may be performed by one module, or the operation of source controller 150 may be performed by more than one module. Additionally, functions may be performed using any suitable logic comprising software, hardware, other logic, or any suitable combination of the preceding.

Figure 6:
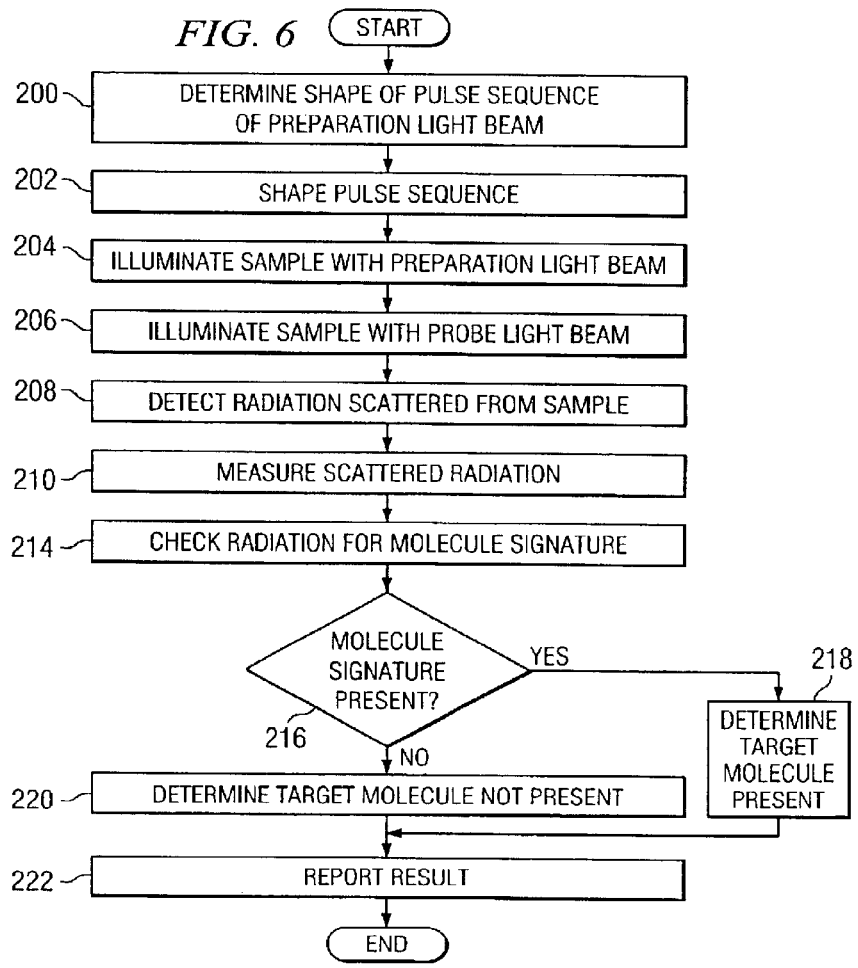
FIG. 6 is a flowchart demonstrating one embodiment of a method for identifying a target molecule.

FIG. 6 is a flowchart illustrating one embodiment of a method for identifying a target molecule. The method begins at step 200, where source controller 150 determines a shape of a pulse sequence of preparation light beam 20. The shape may be selected in order to generate maximized coherence of a target molecule, and may be determined using a learning process. Phase shaper 132 shapes the pulse sequence according to the determined shape at step 202.

Sample 12 is illuminated with preparation light beam 20 at step 204 in order to attempt to generate a maximized coherence of the molecules of sample 12. Sample 12 is illuminated with probe light beam 30 at step 206 in order to generate scattered radiation. If the molecules of sample 12 are at a maximized coherence, the scattered radiation may yield a stronger Raman scattering signal. Detector 134 detects scattered radiation at step 208.

Analyzer 152 measures the scattered radiation at step 210, and checks the scattered radiation to determine whether a signature of the target molecule is present at step 214. If the molecules of sample 12 are at a maximized coherence and the target molecule is present at sample 12, the scattered radiation may exhibit a molecular signature such as a characteristic spectrum corresponding to the target molecule. If the molecule signature is present at step 216, the method proceeds to step 218, where analyzer 152 determines that the target molecule is present. If the molecule signature is not present at step 216, the method proceeds to step 220, where analyzer 152 determines that the target molecule is not present. The results are reported at step 222. After reporting the results, the method terminates.

Modifications, additions, or omissions may be made to the method without departing from the scope of the invention. Additionally, steps may be performed in any suitable order without departing from the scope of the invention.

Certain embodiments of the invention may provide one or more technical advantages. A technical advantage of one embodiment may be that a sample with target molecules is illuminated with a preparation light beam to yield a substantially maximized coherence for the target molecules. The target molecules are identified in accordance with radiation scattered from the sample as a Raman scattering signal. By producing substantially maximized coherence, the Raman scattering signal may be enhanced to provide for more effective analysis of the target molecules.

Although an embodiment of the invention and its advantages are described in detail, a person skilled in the art could make various alterations, additions, and omissions without departing from the spirit and scope of the present invention as defined by the appended claims.

What is claimed is:

1. A method for identifying a molecule of a sample, comprising:

illuminating a sample with a preparation light beam, the preparation light beam operable to initiate a substantially maximized coherence of a target molecule to yield a molecular signature corresponding to the target molecule;

illuminating the sample with a probe light beam, the probe light beam operable to scatter radiation from the sample;

detecting radiation scattered from the sample;
determining whether the radiation exhibits the molecular signature; and
identifying the target molecule in accordance with the determination of whether the radiation exhibits the molecular signature.

2. The method of claim 1, further comprising:
determining a shape of a pulse of the preparation light beam operable to initiate the substantially maximized coherence of the target molecule; and
shaping the pulse of the preparation light beam in accordance with the determined shape.

3. The method of claim 1, wherein the substantially maximized coherence comprises a substantially maximized coherence between a ground state of the target molecule and a first vibrationally excited state of the target molecule.

4. The method of claim 1, wherein the preparation light beam comprises a first femtosecond pulse sequence having a first pulse shape and a second femtosecond pulse sequence having a second pulse shape.

5. The method of claim 1, further comprising:
determining a Raman scattering signal associated with the radiation in response to detecting the radiation scattered from the sample; and
adjusting the preparation light beam to enhance the Raman scattering signal.

6. The method of claim 1, wherein identifying the target molecule in accordance with the determination comprises:
establishing that the target molecule is present if the radiation exhibits the molecular signature; and
establishing that the target molecule is not present if the radiation does not exhibit the molecular signature.

7. A system for identifying a molecule of a sample, comprising:
a source controller operable to:
illuminate a sample with a preparation light beam, the preparation light beam operable to initiate a substantially maximized coherence of a target molecule to yield a molecular signature corresponding to the target molecule; and
illuminate the sample with a probe light beam, the probe light beam operable to scatter radiation from the sample;
a detector operable to detect radiation scattered from the sample; and
an analyzer operable to:
is determine whether the radiation exhibits the molecular signature; and
identify the target molecule in accordance with the determination of whether the radiation exhibits the molecular signature.

8. The system of claim 7, further comprising a pulse shaper operable to:
receive data describing a shape of a pulse of the preparation light beam operable to initiate the substantially maximized coherence of the target molecule; and
shape the pulse of the preparation light beam in accordance with the determined shape.

9. The system of claim 7, wherein the substantially maximized coherence comprises a substantially maximized coherence between a ground state of the target molecule and a first vibrationally excited state of the target molecule.

10. The system of claim 7, wherein the preparation light beam comprises a first femtosecond pulse sequence having a first pulse shape and a second femtosecond pulse sequence having a second pulse shape.

11. The system of claim 7, wherein the analyzer is further operable to:
determine a Raman scattering signal associated with the radiation in response to detecting the radiation scattered from the sample; and
adjust the preparation light beam to enhance the Raman scattering signal.

12. The system of claim 7, wherein the analyzer is further operable to identify the target molecule in accordance with the determination by:
establishing that the target molecule is present if the radiation exhibits the molecular signature; and
establishing that the target molecule is not present if the radiation does not exhibit the molecular signature.

13. Logic for identifying a molecule of a sample, the logic embodied in a medium and operable to:
illuminate a sample with a preparation light beam, the preparation light beam operable to initiate a substantially maximized coherence of a target molecule to yield a molecular signature corresponding to the target molecule;
illuminate the sample with a probe light beam, the probe light beam operable to scatter radiation from the sample;
receive data describing radiation scattered from the sample;
determine whether the radiation exhibits the molecular signature; and
identify the target molecule in accordance with the determination of whether the radiation exhibits the molecular signature.

14. The logic of claim 13, further operable to:
determine a shape of a pulse of the preparation light beam operable to initiate the substantially maximized coherence of the target molecule; and
shape the pulse of the preparation light beam in accordance with the determined shape.

15. The logic of claim 13, wherein the substantially maximized coherence comprises a substantially maximized coherence between a ground state of the target molecule and a first vibrationally excited state of the target molecule.

16. The logic of claim 13, wherein the preparation light beam comprises a first femtosecond pulse sequence having a first pulse shape and a second femtosecond pulse sequence having a second pulse shape.

17. The logic of claim 13, further operable to:
determine a Raman scattering signal associated with the radiation in response to detecting the radiation scattered from the sample; and
adjust the preparation light beam to enhance the Raman scattering signal.

18. The logic of claim 13, further operable to identify the target molecule in accordance with the determination by:
establishing that the target molecule is present if the radiation exhibits the molecular signature; and
establishing that the target molecule is not present if the radiation does not exhibit the molecular signature.

19. A system for identifying a molecule of a sample, comprising:
means for illuminating a sample with a preparation light beam, the preparation light beam operable to initiate a substantially maximized coherence of a target molecule to yield a molecular signature corresponding to the target molecule;

means for illuminating the sample with a probe light beam, the probe light beam operable to scatter radiation from the sample;

means for detecting radiation scattered from the sample;

means for determining whether the radiation exhibits the molecular signature; and means for identifying the target molecule in accordance with the determination of whether the radiation exhibits the molecular signature.

20. A method for identifying a molecule of a sample, comprising:

determining a shape of a pulse of a preparation light beam operable to initiate a substantially maximized coherence of a target molecule to yield a molecular signature corresponding to the target molecule, the substantially maximized coherence comprising a substantially maximized coherence between a ground state of the target molecule and a first vibrationally excited state of the target molecule, the preparation light beam comprising a first femtosecond pulse sequence having a first pulse shape and a second femtosecond pulse sequence having a second pulse shape;

shaping the pulse of the preparation light beam in accordance with the determined shape;

illuminating a sample with the preparation light beam;

illuminating the sample with a probe light beam, the probe light beam operable to scatter radiation from the sample;

detecting radiation scattered from the sample, and determining whether the radiation exhibits the molecular signature;

identifying the target molecule in accordance with the determination of whether the radiation exhibits the molecular signature by establishing that the target molecule is present if the radiation exhibits the molecular signature, and by establishing that the target molecule is not present if the radiation does not exhibit the molecular signature;

determining a Raman scattering signal associated with the radiation in response to detecting the radiation scattered from the sample; and adjusting the preparation light beam to enhance the Raman scattering signal.

* * * * *